United States Patent [19]

Shibatani et al.

[11] 4,222,780

[45] Sep. 16, 1980

[54] ADHESIVE COMPOSITION WITH IMPROVED BONDING AFFINITY FOR HARD HUMAN TISSUES

[75] Inventors: Kyoichiro Shibatani; Ikuo Omura; Junichi Yamauchi, all of Kurashiki, Japan

[73] Assignee: Kuraray Co., Ltd., Kurashiki, Japan

[21] Appl. No.: 898,675

[22] Filed: Apr. 21, 1978

[30] Foreign Application Priority Data

Apr. 27, 1977 [JP] Japan .................................. 52-49378

[51] Int. Cl.$^3$ ....................... C09K 3/00; C08F 130/02
[52] U.S. Cl. ................................ 106/35; 260/998.11; 526/277; 526/278
[58] Field of Search .................... 526/278, 277; 106/35

[56] References Cited

U.S. PATENT DOCUMENTS

| | | | |
|---|---|---|---|
| 3,051,740 | 8/1972 | Abramo | 526/278 |
| 4,044,044 | 8/1977 | Saito | 526/278 |

FOREIGN PATENT DOCUMENTS 933107   8/1963   United Kingdom ..................... 526/278

OTHER PUBLICATIONS

Journal of Dental Research 53, 879–888, 1974.
Journal of Dental Research 56, 943–952, 1977.

*Primary Examiner*—Theodore Morris
*Attorney, Agent, or Firm*—Oblon, Fisher, Spivak, McClelland & Maier

[57] ABSTRACT

An adhesive composition is provided for hard human tissues which contains 0.1 to 10 weight percent as phosphorus of a phosphinic acid compound having the

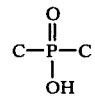

structure. This adhesive composition provides an intimate bond with hard human tissues such as tooth, bone, etc. and has prolonged stability under wet conditions.

10 Claims, No Drawings

ADHESIVE COMPOSITION WITH IMPROVED BONDING AFFINITY FOR HARD HUMAN TISSUES

BACKGROUND OF THE INVENTION

1. Field of the Invention

This invention relates to adhesive compositions for hard human tissues such as tooth, bone, etc. More particularly, this invention relates to adhesive compositions such as adhesives for the treatment of a complex fracture of the bone, filling agents for the fixation of artificial joints, dental adhesives, dental filling materials, etc., which must retain powerful bond strengths under wet conditions.

2. Description of the Prior Art

As the prior art adhesive agents fo the fixation of artificial joints or dental filling agents, there are known mixtures of polymethyl methacrylate with methyl methacrylate, mixtures of bisphenol-A diglycidyl methacrylate with triethylene glycol dimethacrylate, etc. as cured with a radical-generating agent such as a peroxide-amine compound system. However, the cured mass obtained by the known method has little affinity for hard human tissues, the bond strength under wet conditions being as low as about 0 to 5 kg/cm$^2$. For use as preventive filling agents or orthodontic cements, adhesives based on α-cyanoacrylates have been proposed recently to provide an improved adhesion with the dentinal tissue but these adhesives proved to have poor stability in the oral cavity and problems in connection with handling and application. The dental adhesives obtainable by the polymerization of methyl methacrylate with trialkylborons (Japanese Pat. Publications No. 14318/1967 and No. 29195/1970) have only a poor bonding affinity for the enamel, despite their favorable performance with respect to the dentin. It is also known that improved adhesion may be established by adding an addition-polymerizable organic phosphoryl monofluoride compound to a dental adhesive composition (U.S. Pat. No. 3,882,600) but the P-F bond in this compound brings forth safety problems because of the toxic nature of the fluorine compound.

It is further known that improved adhesion may be obtained by adding a divalent phosphoric acid containing a vinyl group allegedly capable of combining itself with the calcium in the tooth as an adhesive composition (Journal of Dental Research 53, 879–888, 1974). This product, however, is practically not sufficiently useful owing to its low bonding affinity.

It has recently been reported that certain monomers having the structure

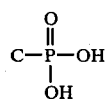

provide a durable and strong bond with the tooth enamel (Journal of Dental Research 56, 943–952, 1977) but the report does not refer to the question of adhesion to the dentin. Some of the present inventors previously discovered that phosphoric or phosphonic acid ester compounds having at least one radical-polymerizable functional group and a

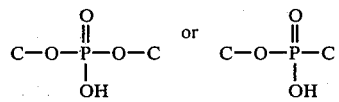

group have an excellent adhesive affinity for the tooth and particularly with respect to the dentin and accordingly filed patent applications U.S. Ser. No. 778,734 and No. 829,486). Nonetheless, we discovered that those phosphoric or phosphonic acid ester compounds leave something to be improved in respect of their stability under wet conditions.

SUMMARY OF THE INVENTION

It is, therefore, an object of this invention to provide an adhesive composition for hard human tissues, which composition provides a strong, lasting and stable bond with both the dentin and enamel of the tooth, bone, etc. and is not injurious to the human body.

It is another object of this invention to provide an adhesive composition for hard human tissues which is of value as a dental filling material.

It is still another object of this invention to provide an adhesive composition which is useful for establishing a bond between the dentinal tissue and a dental filling material.

It is yet another object of this invention to provide an adhesive composition which is useful for establishing a bond between the tooth and an inlay or crown.

Other objects of this invention will become apparent as the following detailed description of the invention proceeds.

The above-mentioned objects may be accomplished by the present adhesive composition containing 0.1 to 10 weight percent, as phosphorus, of a phosphinic acid compound in which the phosphorus atom occurs in the structure

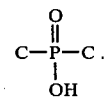

DETAILED DESCRIPTION OF THE PREFERRED EMBODIMENTS

The phosphinic acid compound that is employed according to this invention may be any compound that has the structure

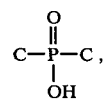

although the compounds represented by the following formula (1) are particularly preferred.

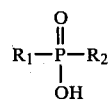

(1)

In the above formula, $R_1$ and $R_2$, respectively, designate an organic compound residue which contains 1 to 25 carbon atoms and the molecular weight of which is not more than 500, at least one of $R_1$ and $R_2$ containing a polymerizable group. As examples of said polymerizable group may be mentioned epoxy, hydroxyl, amino, carboxyl, etc. which are capable of providing an increased molecular weight by undergoing an epoxy ring opening reaction, amidation, polyesterification, urethanation or other ring-opening, polycondensation or addition-polymerization reaction, and vinyl groups which are able to undergo addition-polymerization to provide an increased molecular weight are particularly desirable. The vinyl groups preferably have styrenic, acrylic or methacrylic structures. It is still more preferable that at least one of $R_1$ and $R_2$ has a phenyl or naphthyl group. Such a phosphinic acid compound may be contained as a monomer in the adhesive composition or/and may be contained in the form of a homopolymer or a copolymer with other monomers. Such polymers normally have molecular weights not less than 1000 and not more than a million.

By virtue of containing such a phosphinic acid compound, the adhesive composition of this invention not only displays an excellent adhesive affinity for hard human tissues under wet conditions but, because of the excellent resistance of the phosphinic acid compound to hydrolysis, retains its high bond strength over an extended period of time.

Compared with the prior art phosphoric or phosphonic acid ester compounds, the phosphinic acid compounds of this invention have excellent practical advantages. Thus, the latter have improved shelf lives, being free from discoloration on prolonged storage, and improved resistance to hydrolysis and provide a lasting bond strength.

As examples of phosphinic acid compounds according to this invention, the following compounds may be mentioned.

Examples of compounds which do not contain polymerizable groups:

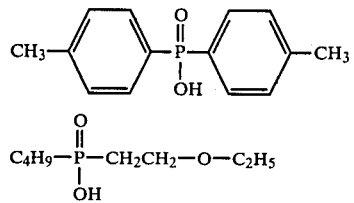

Examples of compounds containing polymerizable groups other than a vinyl group, and polymers obtainable therefrom:

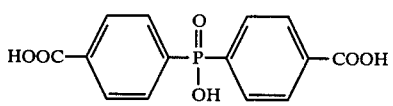

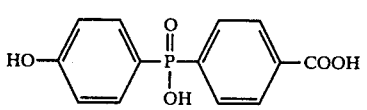

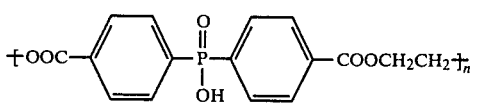

Examples of compounds containing vinyl groups:

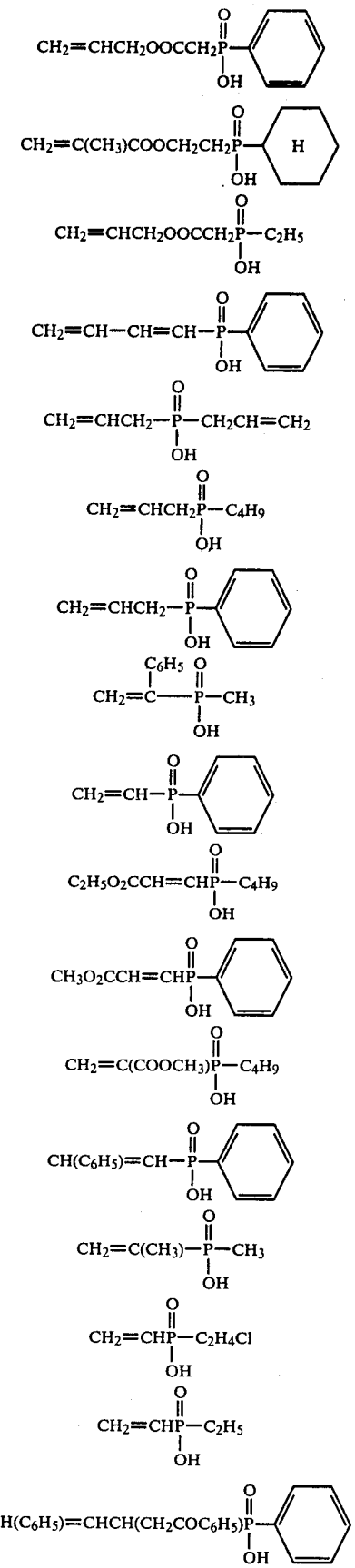

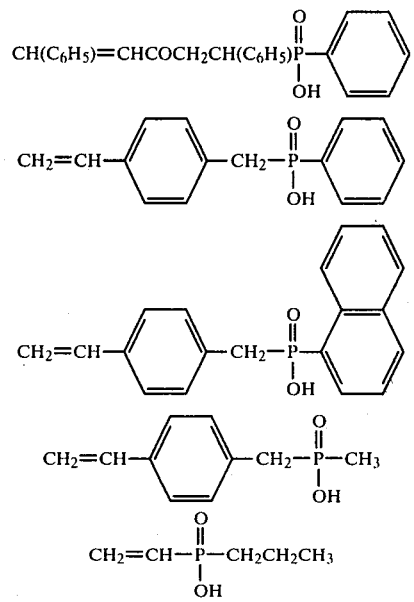

The general method for producing compounds of the formula:

$$R_1-\underset{\underset{OH}{|}}{\overset{\overset{O}{\|}}{P}}-R_2$$

as follows.

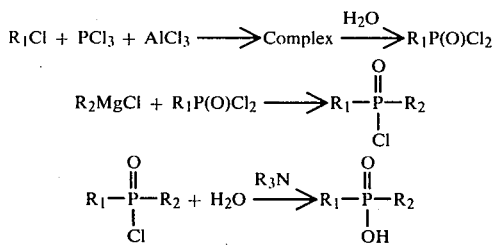

The detailed reaction conditions may be selected with reference to the following literature.

"Organophosphorous Monomers and Polymers" by Ye. L. Gefter (Pergamon Press, New York, 1962)

"Organophosphorus Compounds" by G. M. Kosolapoff (Wiley, New York, 1950)

"Organophosphorus Compounds" by M. Ota (Gihodo, 1971, in Japanese language)

In accordance with this invention, some of the OH groups in the

structure may exist in the form of a salt, e.g. as ONa, although the degree of such substitution is preferably such that the residual content of phosphorus in the form of

in the adhesive composition is not less than 0.1 percent by weight. The salt may be any of various metal salts and amine salts and is useful for the purpose of mitigating the possible irritation of the free acid to the human body.

An improved adhesion is obtained when such a phosphinic acid compound is contained in an amount not less than 0.1 weight percent as phosphorus (based on the adhesive composition), preferably in a proportion not less than 0.3 weight percent on the same basis. The adhesive strength rather tends to drop as the phosphorus content increases beyond 10 weight percent.

By adding a phosphinic acid compound to a conventional adhesive composition, adhesive agent or cement for hard human tissues, an improvement in the adhesive affinity of such composition or agent can be realized. Particularly, said phosphinic acid compound preferably contains a vinyl group and is copolymerized, when the bonding operation is carried out, with some other copolymerizable monomer which may also be previously incorporated in the adhesive composition. As examples of said copolymerizable monomer may be mentioned acrylic acid, methacrylic acid and their esters, acrylamides, styrene, vinyl acetate and so on. In view of the physical properties of the resultant polymers, these copolymerizable monomers preferably contain not more than 30 carbon atoms per vinyl group. Thus, it is preferable that, in the case of a monovinyl monomer, it contain up to 30 carbon atoms and that, in the case of a divinyl monomer, it contain up to 60 carbon atoms. Particularly preferred compounds among such monomers are acrylic (or methacrylic) acid esters such as monovinyl (meth) acrylates, e.g. methyl (meth)acrylate, ethyl (meth)acrylate, propyl (meth)acrylate, hydroxyethyl (meth)acrylate, hydroxypropyl (metha)acrylate, diethylene glycol (meth)acrylate, triethylene glycol (metha)-acrylate, the monoester of trimellitic acid with hydroxyethyl (meth)acrylate, etc. and polyfunctional (meth)acrylates, e.g. ethylene glycol di(meth)acrylate, di, tri- or tetraethylene glycol di(meth)acrylate, glycerin tri(meth)acrylate, neopentyl glycol di(meth)acrylate, butanediol di(meth)acrylate, trimethylolpropane (tri(meth)acrylate, tetramethylolmethane tetra(meth) acrylate, bisphenol-A di(meth)acrylate, bisphenol-A diglycidyl (meth)acrylate, 2,2-bis(4-methacryloxyethoxyphenyl)propane and so on. The copolymerizing ratio of the phosphinic compound to such copolymerizable monomer or monomers is optional but in consideration of the water resistance of the resultant polymers, the proportion of the phosphinic acid compound is preferably not more than 10 mol percent.

As to polymerization initiators for the phosphinic acid compound containing a vinyl group, such catalyst systems of the room temperature cure type as amine-peroxide, amine-peroxide-sulfinic acid salt, peroxide-sulfinic acid and trialkylboron may be mentioned as well as ultraviolet sensitizers. Particularly, the use of a curing system comprising a peroxide, amine and sulfinate is desirable.

As components to be employed in the adhesive components of this invention, in addition to the phosphinic acid compound, other polymers, fillers (quartz, glass, etc.), metal oxides, stabilizers, plasticizers and so forth may be mentioned, which are conventionally used in the field of adhesive agents for the hard tissues of the human body. One may optionally select suitable components from among such components.

In applying the adhesive compositions of this invention to the hard tissues of the human body, they may be coated over or filled into the hard tissues in a pasty or liquid state, and then the setting or curing operation is carried out, whereby the function of the adhesive is fulfilled. The above setting and curing methods may be of the following variety. There may for example be mentioned increasing the molecular weight by binding with a metal, a metal oxide and so on, network forming, evaporation of a solvent and polymerization of the monomer.

Setting by means of a metal oxide, for instance, is a preferred procedure that may be applied when the intended use is as a joining cement, while the procedure involving the evaporation of a solvent is suitable when the product is used as an adhesive primer in the filling of a resin compound into a tooth cavity. For these purposes, the phosphinic acid ester compound of this invention having the

structure is sufficiently useful even if it does not contain a polymerizable group, provided that said compound has a fairly high molecular weight. The method of setting and curing of the adhesive composition which depends on the polymerization of monomers is suited when the product is used as a bone cement, dental filling resin or the like. In these applications, the molecule containing the

structure preferably contains at least one polymerizable group.

The compound is added in a monomeric form to the adhesive composition and polymerized at the time of curing.

Now, the adhesive composition of this invention will be described in detail with particular reference to dental filling materials and adhesive agents for bonding a dental filling material to the tooth, which are preferred uses of the invention. When the adhesive composition is employed as a dental filling material, a filling material with an improved bonding strength can be obtained by admixing the phosphinic acid compound with a conventional filling agent. A phosphinic acid containing a vinyl group is preferably employed and admixed with a copolymerizable monomer (or monomers), filler and initiator to prepare the filling material. As examples of the copolymerizable monomer, use may be made of methacrylic acid esters containing aromatic groups such as bisphenol-A diglycidyl methacrylate, bisphenol-A dimethacrylate, etc. and polyfunctional methacrylic acid esters such as ethylene glycol dimethacrylate, triethylene glycol dimethlacrylate, neopentyl glycol dimethacrylate, etc. As the fillers, silanated quartz powder and fused silica powder with grain sizes from 1 to 50μ, colloidal silica with diameters not more than 1μ and high polymer powders with diameters in the range of 1 to 200μ, which are conventionally employed, may be utilized either singly or as a mixture. The initiator may be selected from among the aforementioned initiators of room temperature cure type. Since such initiator is a binary or ternary system and its decomposition starts immediately upon admixing, it is made available in two or three independent packages.

When the adhesive composition of this invention is used as an adhesive agent for bonding a dental filling material to the tooth, the composition is coated over the wall of the cavity in the tooth and, then, the filling material is filled into the cavity to repair the tooth. In this manner, a high bond strength is obtained between the tooth and the filling material. The above adhesive agent is prepared by dissolving a vinyl-containing phosphinic acid compound of this invention in a volatile organic solvent with a boiling point of not more than 80° C. (e.g. ethanol, ethyl ether, etc.) or in another copolymerizable monomer (e.g. a metharylic acid ester). Preferably, the aforementioned initiator of room temperature cure type is incorporated in the adhesive agent. This means that said adhesive agent is made available in two or three independent packages, with the phosphinic acid compound of this invention being contained in at least one of said packages. This adhesive agent, taken together with the conventional dental filling material, provides an orthondontic restoration material having a considerably increased adhesive strength and a significantly improved shelf life over the conventional orthodontic restoration material. Moreover, the dental filling material containing a phosphinic acid compound according to this invention may be used as an orthodontic restoration material in conjunction with a conventional dental adhesive.

Because this invention may, thus, be practiced by the application of the conventional clinical techniques without any significant modification, the dentist and others in the profession can easily use the adhesive composition of this invention. Furthermore, the adhesive composition of this invention provides a strong bond strength with respect to hard human tissues such as tooth and bone, which has never been accomplished by the prior art and this bond strength is fully retained over a long period of time under wet conditions such as those encountered in the oral cavity and in the body.

The following examples are intended to illustrate this invention in further detail without limiting its scope thereto.

EXAMPLE 1

By the procedures described below, vinylbenzylphenylphosphinic acid was synthetized and an adhesive composition for hard human tissues was prepared.

(1) Synthesis of vinylbenzylphenylphosphinic acid

A three-necked flask of 1 l capacity was charged with 4.86 g of magnesium, 80 ml of dry tetrahydrofuran and 50 mg of iodine. Then, by means of a dropping funnel, a solution of 30.6 g of p-chloromethylstyrene in 300 ml of dry tetrahydrofuran was added dropwise and the reaction was carried out at room temperature. When the magnesium had substantially disappeared, 39 g of phenylsulfonic acid dichloride

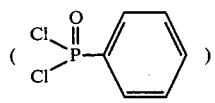

was added dropwise with ice-cooling. After the dropwise addition had been completed, the reaction mixture was heated once to the boiling point of tetrahydrofuran and held at that temperature for 10 minutes. Then, at room temperature, a solution of 40 ml of concentrated hydrochloric acid in a mixture of 200 ml water and 200 g ice was added in small installments. The reaction mixture was extracted with 300 ml of ethyl ether and a mixture of 22.3 g of triethylamine and 10.8 g of water was added to the extract. The precipitate was filtered, followed by extractive purification to obtain 15 g of the contemplated phosphinic acid compound.

(2) Production of an adhesive composition for hard human tissues

Using the phosphinic acid compound prepared above, a two-package adhesive composition consisting of a powder and a liquid component was produced.

Package A (liquid component): 80 weight parts of methyl methacrylate, 10 wt. parts of ethylene glycol dimethacrylate, 10 wt. parts of vinylbenzylphenylphosphinic acid

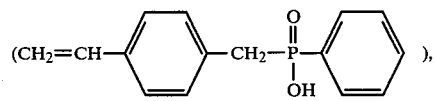

1 wt. part of N,N-diethanol-p-toluidine and, as a polymerization inhibitor, 0.02 wt. part of hydroquinone monomethyl ether were admixed to prepare a solution.

Package B (powder component): 100 weight parts of polymethyl methacrylate (mol. wt. 130,000), 2 wt. parts of benzoylperoxide and 3 wt. parts of sodium benzenesulfinate were evenly admixed to prepare a powder component.

(3) Determination of adhesive strength

A pair of wet bars of ivory, 10 mm by 10 mm by 100 mm, were prepared and the end surfaces (10 mm by 10 mm each) of the bars were wiped free of moisture with a paper wiper. Equal weight parts of Packages A and B were admixed and the mixture was coated over said end surfaces. The two bars were joined end to end. The adhesive mixture made up of the two packages set at room temperature within a few minutes. Then, the assembly was immersed in water at 37° C. for 24 hours and the bars were pulled apart at a rate of 2 mm/min. to measure the bond strength. The result showed an excellent bond strength, i.e. 74 kg/cm$^2$. The same bond strength was still found after the assembly of bars had been kept immersed in water at 37° C. for 6 months, thus indicating that the adhesive composition of this invention was excellent in the retention of bond strength. A control adhesive composition obtained in the same manner as above except that vinylbenzylphenylphosphinic acid was omitted from Package A was found to have a bond strength of as low as about 2 kg/cm$^2$ as similarly measured.

EXAMPLE 2

Using the following materials in the indicated amounts, a two-liquid adhesive primer and a two-paste composite resin were each produced in the following manner.

(1) Adhesive primer

Package C:

| | |
|---|---|
| Bisphenol-A diglycidyl methacrylate | 30 wt. parts |
| Triethylene glycol dimethacrylate | 20 wt. parts |
| Neopentyl glycol dimethacrylate | 20 wt. parts |
| 2-Hydroxyethyl methacrylate | 20 wt. parts |
| Benzoyl peroxide | 2 wt. parts |
| Hydroquinone monomethyl ether | 0.05 wt. part |

To the above mixture was added 10 weight parts of vinylbenzylphenylphosphinic acid according to this invention. A control primer was prepared in the same manner as above but using 2-methacryloxyethylphenylphosphoric acid or 2-methacryloxyethylphosphoric acid in lieu of the above phosphinic acid.

Package D:

| | |
|---|---|
| Ethanol | 100 wt. parts |
| Sodium benzenesulfinate | 3 wt. parts |
| N,N-diethanol-p-toluidine | 1 wt. part |

(2) Composite Resin

Package E:

| | |
|---|---|
| Bisphenol-A diglycidyl methacrylate | 18.3 wt. parts |
| Triethylene glycol dimethacrylate | 6.1 wt. parts |
| Silanated quartz powder | 74.4 wt. parts |
| Colloidal silica | 1.0 wt. part |
| N,N-diethanol-p-toluidine | 0.2 wt. part |
| Hydroquinone monomethyl ether | 0.02 wt. part |
| 2,6-Di-t-butyl-p-cresol | 0.02 wt. part |

Package F:

| | |
|---|---|
| Bisphenol-A diglycidyl methacrylate | 18.0 wt. parts |
| Triethylene glycol dimethacrylate | 6.0 wt. parts |
| Silanated quartz powder | 74.6 wt. parts |
| Colloidal silica | 1.0 wt. part |
| Benzoyl peroxide | 0.4 wt. part |
| Hydroquinone monomethyl ether | 0.02 wt. part |
| 2,6-Di-t-butyl-p-cresol | 0.04 wt. part |

(3) Determination of bond strength and shelf life

Wet ivory bars similar to those described in Example 1 were prepared. A drop each of Package C and Package D was taken in a glass dish and, after blending, the mixture was coated on the end faces of the ivory bars with a small-sized brush. The coated faces were blown with compressed air to evaporate the ethanol from the primer. Then, equal weights of materials were taken from Packages E and F and mixed well. The mixture was sandwiched between said end faces and the bars were joined end to end. Thereafter, the assembly was immersed in water at 37° C. for 24 hours and the bond strength was measured as in Example 1. The results are shown in Table 1. On the other hand, Adhesive Primer C was stored as packaged at room temperature for 6 months to investigate its shelf life. The results are also shown in Table 1. Such shelf lives were evaluated on the basis of discoloration.

Table 1

| No. | Phosphinic acid in Package C | Bond strength (kg/cm$^2$) | Resistance to discoloration |
|---|---|---|---|
| 1-1 | Vinylbenzylphenyl-phosphinic acid<br>$(CH_2=CH-\phenyl-CH_2-P(=O)(OH)-\phenyl)$ | 108 | Not colored |
| 1-2 | 2-Methacryloxyethylphenyl-phosphoric acid<br>$CH_2=C(CH_3)-COOCH_2CH_2O-P(=O)(OH)-O-\phenyl$ | 121 | Yellowish brown |
| 1-3 | 2-Methacryloxyethyl-phosphoric acid<br>$(CH_2=C(CH_3)-COOCH_2CH_2O-P(=O)(OH)-OH)$ | 19 | Not colored |

It will be apparent from Table 1 that the adhesive composition of this invention (1—1) provided an excellent bond strength with respect to wet ivory bars and had a long shelf life showing high stability without discoloration even on prolonged storage. This compares with the prior art composition (1—2) containing a phosphoric acid ester compound, which had a high bond strength with respect to wet ivory bars but displayed only a poor shelf life with the package containing the above compound suffering discoloration on prolonged storage. In the case of (1—3) containing a dibasic phosphoric acid ester compound, the composition had only a very low adhesive affinity for wet ivory bars, thus being considerably inferior to the adhesive composition of this invention.

EXAMPLE 3

An adhesive composition for hard human tissues which consisted of the following two packages was prepared as follows. Package G (liquid component): 80 wt. parts of methyl methacrylate, 10 wt. parts of ethylene glycol dimethacrylate, 10 wt. parts of vinylphenylphosphinic acid

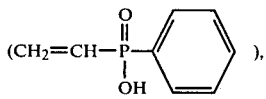

1 wt. part of N,N-diethanol-p-toluidine and 0.02 wt. part of hydroquinone monomethyl ether were admixed to prepare a solution.
Package H (powder component):
100 wt. parts of polymethyl methacrylate powder (mol. wt. 130,000), 2 wt. parts of benzoyl peroxide and 3 wt. parts of sodium benzenesulfinate were evenly admixed.

Small amounts of the contents of Packages G and H were mixed and applied to wet ivory bars and the bond strength was measured as in Example 1. The bond strength was found to be 42 kg/cm$^2$.

EXAMPLE 4

To 0.5 ml of a liquid consisting of 80 wt. parts of methyl methacrylate, 15 wt. parts of triethylene glycol dimethacrylate, 5 wt. parts of vinylbenzylphenylphosphinic acid

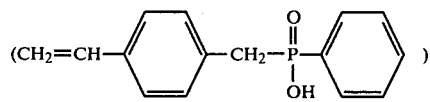

and 0.03 parts of hydroquinone monomethyl ether was added 0.02 ml of tri-n-butylborane as a polymerization initiator. After thorough mixing, 0.5 g of polymethyl methacrylate powder was added, followed by further mixing. The resultant adhesive composition was applied to wet ivory bars and the bond strength was measured as in Example 1. The bond strength was found to be 106 kg/cm$^2$.

EXAMPLE 5

The following two packages were produced for use as an adhesive composition for hard human tissues. Package I (liquid component): To a mixture of 90 wt. parts of methyl methacrylate, 10 wt. parts of allylphenylphosphinic acid

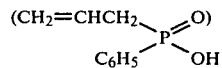

and 0.5 wt. part of dimethyl-p-toluidine was added 0.02 wt. part of hydroquinone monomethyl ether as a polymerization inhibitor. Then, 0.005 wt. part of 2-hydroxy-4-methoxybenzophenone as an ultraviolet absorber was further added and admixed to prepare Package I. Package J (powder component): 100 wt. parts of polymethyl methacrylate (mol. wt. 130,000), 1.3 wt. parts of benzoyl peroxide and 1.5 wt. parts of sodium p-toluenesulfinate were admixed.

When aliquots of Packages I and J were admixed, the mixture cured at room temperature within a few minutes. An extracted human molar was divided in half and the viscous mixture of Packages I and J was applied to the ground mating surfaces of the halves. When the halves were joined to restore the original molar, they were intimately bonded. A hole was drilled in each of the halves and the joined molar specimen was immersed in water at 37° C. for 6 months with a weight of 1 kg hung from the specimen. It was found that the bond strength was not affected by the above treatment.

EXAMPLE 6

The following two packages were prepared as an adhesive primer for application between a dental filling composite resin and a tooth. Package K (liquid component): 40 wt. parts of bisphenol-A diglycidyl methacrylate, 50 wt. parts of triethylene glycol dimethacrylate, 10 wt. parts of styrylmethylphosphinic acid

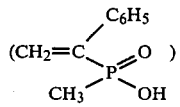

and 1.5 wt. parts of benzoyl peroxide were admixed to prepare Package K. Package L (liquid component): 40 wt. parts of bisphenol-A diglycidyl methacrylate, 60 wt. parts of hydroxyethyl methacrylate, 3 wt. parts of sodium benzenesulfinate and 2 wt. parts of N,N-diethanol-p-toluidine were admixed to prepare Package L.

When Packages K and L were admixed, the adhesive system having a strong adhesive affinity for hard human tissues consisting of collagen and calcium apatite was activated and cured itself to give a firm bond at room temperature within a few minutes. A simple cavity was formed in an extracted human tooth and the cavity wall of enamel was treated with a 50% aqueous solution of phosphoric acid, rinsed with water and dried. One drop each of Package K and Package L (substantially, equal portions) was taken, mixed in a glass dish and applied to the enamel and dentinal parts of said tooth cavity with a small ball of cotton. Then, a dental filling composite resin (Adaptic®, Johnson & Johnson) was further filled into the cavity. The adhesive composition made up of Packages K and L adhered intimately to both the tooth and the composite resin, providing an excellent marginal sealing effect. The tooth filled by the above technique was subjected to a percolation test in which the tooth was alternatingly dipped into a water bath containing fuchsine dissolved therein at 4° C. and into a similar dye-water bath at 60° C. at intervals of 1 minute for a total of 100 times. The result showed no infiltration of the dye between the filling material and the tooth.

What we claim as our invention:

1. An adhesive composition for cementing teeth or bones, comprising
   (1) a phosphinic acid compound wherein the substituents on the phosphorus atom occur as follows:

wherein said phosphinic acid compound is a compound of the formula:

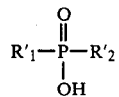

wherein $R'_1$ and $R'_2$ each represent an organic compound residue containing 1 to 25 carbon atoms and having a molecular weight of up to 500, and at least one of $R'_1$ and $R'_2$ contains a vinyl group, or (2) a polymer containing said phosphinic acid compound as a component unit, wherein said adhesive composition contains 0.1 to 10 weight percent as phosphorus of said phosphinic acid compound.

2. The adhesive composition of claim 1, comprising said phosphinic acid compound and a polymerization initiator comprising a peroxide, an amine and a sulfinate.

3. A dental filling material having an improved adhesive affinity for the tooth, comprising: an admixture of a filler with an adhesive composition comprising (1) a phosphinic acid compound wherein the substituents on the phosphorus atom occur as follows:

and wherein said phosphinic acid compound is a compound of the formula:

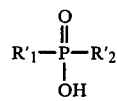

wherein $R'_1$ and $R'_2$ each represent an organic compound residue containing 1 to 25 carbon atoms and having a molecular weight of up to 500, and at least one of $R'_1$ and $R'_2$ contains a vinyl group, (2) a copolymerizable monomer comprising a methacrylic acid ester and (3) a polymerization initiator, wherein said adhesive composition contains 0.1 to 10 weight percent as phosphorus of said phosphinic acid compound.

4. A dental adhesive primer for bonding a dental filling material to the tooth, comprising: (1) a phosphinic acid compound wherein the substituents on the phosphorus atom occur as follows:

and wherein said phosphinic acid compound is a compound of the formula:

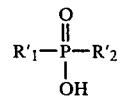

wherein $R'_1$ and $R'_2$ each represent an organic compound residue containing 1 to 25 carbon atoms and having a molecular weight of up to 500, and at least one of $R'_1$ and $R'_2$ contains a vinyl group, and (2) a copolymerizable monomer comprising a methacrylic acid ester, wherein said adhesive primer contains 0.1 to 10 weight percent as phosphorus of said phosphinic acid compound.

5. The dental adhesive primer of claim 1, wherein said methacrylic acid ester is methyl methacrylate, hydroxyethyl methacrylate, bisphenol-A diglycidyl methacrylate, bisphenol-A dimethacrylate, ethylene glycol dimethacrylate, triethylene glycol dimethacrylate or neopentyl glycol dimethacrylate.

6. The dental adhesive primer of claim 4, additionally comprising a polymerization initiator.

7. The dental adhesive primer of claim 6, wherein said primer comprises at least two independent packages, at least one of said packages containing said phosphinic acid compound.

8. The dental adhesive primer of claim 7, wherein one of said packages comprises said phosphinic acid compound and a volatile organic solvent having a boiling point of not higher than 80° C.

9. The dental adhesive primer of claim 7, wherein one of said packages comprises said phosphinic acid compound and said copolymerizable monomer.

10. An orthodontic restoration material, comprising: a dental filling material and a dental adhesive agent for bonding said filling material to the tooth, at least one of said filling material and said dental adhesive agent comprising an adhesive composition containing (1) a phosphinic acid compound wherein the substituents on the phosphorus atom occur as follows:

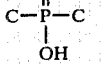

and wherein said phosphinic acid compound is a compound of the formula:

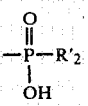

wherein $R'_1$ and $R'_2$ each represent an organic compound residue containing 1 to 25 carbon atoms and having a molecular weight of up to 500, and at least one of $R'_1$ and $R'_2$ contains a vinyl group, and (2) a copolymerizable monomer comprising a methacrylic acid ester, wherein said adhesive composition contains 0.1 to 10 weight percent as phosphorus of said phosphinic acid compound.

* * * * *

UNITED STATES PATENT AND TRADEMARK OFFICE
CERTIFICATE OF CORRECTION

PATENT NO. : 4,222,780
DATED : September 16, 1980
INVENTOR(S) : Kyoichiro Shibatani et al It is certified that error appears in the above-identified patent and that said Letters Patent are hereby corrected as shown below:

Column 1, line 18, delete "fo" and insert --for--.

Column 8, line 32, delete "orthondontic" and insert --orthodontic--.

Column 8, line 58, delete "synthetized" and insert --synthesized--.

Column 8, line 68, delete "phenylsulfonic" and insert --phenylphosphonic--.

Signed and Sealed this

Seventh Day of July 1981

[SEAL]

Attest:

RENE D. TEGTMEYER

Attesting Officer

Acting Commissioner of Patents and Trademarks